(12) United States Patent  (10) Patent No.: US 7,265,549 B2
Alvarez et al.  (45) Date of Patent: Sep. 4, 2007

(54) SCANNING A BAND OF FREQUENCIES USING AN ARRAY OF HIGH TEMPERATURE SUPERCONDUCTOR SENSORS TUNED TO THE SAME FREQUENCY

(75) Inventors: Robby L. Alvarez, Newark, DE (US); James D. McCambridge, Swarthmore, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/118,962

(22) Filed: Apr. 29, 2005

(65) Prior Publication Data

US 2005/0248345 A1 Nov. 10, 2005

Related U.S. Application Data

(60) Provisional application No. 60/566,953, filed on Apr. 30, 2004.

(51) Int. Cl.
*G01V 3/00* (2006.01)
(52) U.S. Cl. .................. 324/310; 324/300; 324/307; 324/318
(58) Field of Classification Search ............ None
See application file for complete search history.

(56) References Cited

U.S. PATENT DOCUMENTS

| 3,373,348 | A |   | 3/1968  | Vanier et al. |
|-----------|---|---|---------|---------------|
| 3,764,892 | A |   | 10/1973 | Rollwitz |
| 4,072,768 | A |   | 2/1978  | Fraser et al. |
| 4,514,691 | A |   | 4/1985  | De Los Santos et al. |
| 5,036,279 | A |   | 7/1991  | Jonsen |
| 5,135,908 | A |   | 8/1992  | Yang et al. |
| 5,206,592 | A |   | 4/1993  | Buess et al. |
| 5,233,300 | A |   | 8/1993  | Buess et al. |
| 5,258,710 | A | * | 11/1993 | Black et al. ............. 324/309 |
| 5,262,394 | A |   | 11/1993 | Wu et al. |
| 5,276,398 | A |   | 1/1994  | Withers et al. |
| 5,351,007 | A |   | 9/1994  | Withers et al. |
| 5,418,213 | A |   | 5/1995  | Tanaka et al. |
| 5,457,385 | A |   | 10/1995 | Sydney et al. |
| 5,583,437 | A |   | 12/1996 | Smith et al. |
| 5,585,723 | A |   | 12/1996 | Withers |
| 5,592,083 | A |   | 1/1997  | Magnuson et al. |

(Continued)

FOREIGN PATENT DOCUMENTS

EP  0 426 851  5/1991

(Continued)

OTHER PUBLICATIONS

Miller, et al., "Performance of a High-Temperature Superconducting Probe for In Vivo Microscopy at 2.0 T", Magnetic Resonance in Medicine, (1999) pp. 72-79, vol. 41.

(Continued)

*Primary Examiner*—Brij Shrivastav
*Assistant Examiner*—Tiffany A. Fetzner

(57) ABSTRACT

The methods of the invention for scanning a band of frequencies using a nuclear quadrupole resonance detection system with an array of high temperature superconductor sensors to detect nuclear quadrupole resonance signals improve the nuclear quadrupole resonance detection system performance.

18 Claims, 3 Drawing Sheets $t_1$ $t_2$ $t_3$ $t_4$

U.S. PATENT DOCUMENTS

| | | |
|---|---|---|
| 5,594,338 A | 1/1997 | Magnuson |
| 5,656,937 A | 8/1997 | Cantor |
| 5,661,400 A | 8/1997 | Plies et al. |
| 5,750,473 A | 5/1998 | Shen |
| 5,751,146 A | 5/1998 | Hrovat |
| 5,804,967 A | 9/1998 | Miller et al. |
| 5,814,987 A | 9/1998 | Smith et al. |
| 5,814,989 A | 9/1998 | Smith et al. |
| 5,814,992 A | 9/1998 | Busse-Gravitz et al. |
| 5,872,080 A | 2/1999 | Arendt et al. |
| 5,952,269 A | 9/1999 | Ma et al. |
| 5,973,495 A | 10/1999 | Mansfield |
| 5,986,455 A | 11/1999 | Magnuson |
| 5,999,000 A | 12/1999 | Srinivasan |
| 6,025,719 A | 2/2000 | Anderson |
| 6,054,856 A | 4/2000 | Garroway et al. |
| 6,088,423 A | 7/2000 | Krug et al. |
| 6,091,240 A | 7/2000 | Smith et al. |
| 6,104,190 A | 8/2000 | Buess et al. |
| 6,108,569 A | 8/2000 | Shen |
| 6,150,816 A | 11/2000 | Srinivasan |
| 6,166,541 A | 12/2000 | Smith et al. |
| 6,169,399 B1 | 1/2001 | Zhang et al. |
| 6,194,898 B1 | 2/2001 | Magnuson et al. |
| 6,201,392 B1 | 3/2001 | Anderson et al. |
| 6,218,943 B1 | 4/2001 | Ellenbogen |
| 6,242,918 B1 | 6/2001 | Miller et al. |
| 6,291,994 B1 | 9/2001 | Kim et al. |
| 6,335,622 B1 | 1/2002 | James et al. |
| 6,370,404 B1 | 4/2002 | Shen |
| D459,245 S | 6/2002 | Power |
| 6,420,872 B1 | 7/2002 | Garroway et al. |
| 6,486,838 B1 | 11/2002 | Smith et al. |
| 6,538,445 B2 | 3/2003 | James et al. |
| 6,541,966 B1 | 4/2003 | Keene |
| 6,556,013 B2 | 4/2003 | Withers |
| 6,566,873 B1 | 5/2003 | Smith et al. |
| 6,590,394 B2 | 7/2003 | Wang et al. |
| 6,617,591 B1 | 9/2003 | Simonson et al. |
| 6,653,917 B2 | 11/2003 | Kang et al. |
| 6,751,489 B2 | 6/2004 | Shen |
| 6,751,847 B1 | 6/2004 | Brey et al. |
| 6,777,937 B1 | 8/2004 | Miller et al. |
| 6,819,109 B2 | 11/2004 | Sowers et al. |
| 6,822,444 B2 | 11/2004 | Lai |
| 6,847,208 B1 | 1/2005 | Crowley et al. |
| 6,952,163 B2 | 10/2005 | Huey et al. |
| 6,956,476 B2 | 10/2005 | Buess et al. |
| 6,958,608 B2 | 10/2005 | Takagi et al. |
| 7,049,814 B2 | 5/2006 | Mann |
| 7,106,058 B2 * | 9/2006 | Wilker et al. ............... 324/300 |
| 2002/0068882 A1 | 6/2002 | Shen |
| 2002/0153891 A1 | 10/2002 | Smith et al. |
| 2002/0156362 A1 | 10/2002 | Bock et al. |
| 2002/0169374 A1 | 11/2002 | Jevtic |
| 2002/0190715 A1 | 12/2002 | Marek |
| 2003/0020553 A1 | 1/2003 | Gao et al. |
| 2003/0062896 A1 | 4/2003 | Wong et al. |
| 2003/0071619 A1 | 4/2003 | Sauer et al. |
| 2003/0119677 A1 | 6/2003 | Qiyan et al. |
| 2003/0136920 A1 | 7/2003 | Flores et al. |
| 2004/0124840 A1 | 7/2004 | Reykowski |
| 2004/0222790 A1 | 11/2004 | Kami et al. |
| 2004/0251902 A1 | 12/2004 | Takagi et al. |
| 2005/0104593 A1 * | 5/2005 | Laubacher .................. 324/322 |
| 2005/0122109 A1 * | 6/2005 | Wilker et al. ............... 324/318 |
| 2005/0140371 A1 | 6/2005 | Alvarez et al. |
| 2005/0146331 A1 | 7/2005 | Flexman et al. |
| 2005/0206382 A1 * | 9/2005 | Laubacher et al. ......... 324/318 |
| 2005/0248345 A1 * | 11/2005 | Alvarez et al. ............. 324/310 |
| 2005/0258831 A1 * | 11/2005 | Alvarez et al. ............. 324/310 |
| 2005/0264289 A1 * | 12/2005 | Alvarez et al. ............. 324/310 |
| 2005/0270028 A1 * | 12/2005 | Alvarez et al. ............. 324/311 |
| 2006/0012371 A1 * | 1/2006 | Laubacher et al. ......... 324/322 |
| 2006/0038563 A1 | 2/2006 | Cisholm et al. |
| 2006/0082368 A1 | 4/2006 | McCambridge |
| 2006/0119360 A1 | 6/2006 | Yamamoto et al. |

FOREIGN PATENT DOCUMENTS

| | | |
|---|---|---|
| EP | 1 122 550 A1 | 8/2001 |
| EP | 1 168 483 | 1/2002 |
| EP | 1 416 291 | 5/2004 |
| EP | 1 477 823 A | 11/2004 |
| GB | 2 286 248 | 8/1995 |
| GB | 2 289 344 | 11/1995 |
| JP | 05 269108 | 10/1993 |
| JP | 07 265278 | 10/1995 |
| WO | WO92/17793 | 10/1992 |
| WO | WO92/17794 | 10/1992 |
| WO | WO92/19978 | 11/1992 |
| WO | WO92/21989 | 12/1992 |
| WO | WO94/05022 | 3/1994 |
| WO | WO95/34096 | 12/1995 |
| WO | WO96/39636 | 12/1996 |
| WO | WO 96/39636 | 12/1996 |
| WO | WO96/39638 | 12/1996 |
| WO | WO98/37438 | 8/1998 |
| WO | WO98/54590 | 12/1998 |
| WO | WO99/45409 | 9/1999 |
| WO | WO99/50689 | 10/1999 |
| WO | WO 00/70356 | 11/2000 |
| WO | WO 02/082115 A2 | 10/2002 |
| WO | WO 02/098364 | 12/2002 |
| WO | WO 03/014700 | 2/2003 |
| WO | WO 03/040761 | 5/2003 |
| WO | WO 03/096041 | 11/2003 |
| WO | WO 04/001454 A | 12/2003 |
| WO | WO 2004/102596 | 11/2004 |
| WO | WO 2005/059582 A1 | 6/2005 |

OTHER PUBLICATIONS

W.H. Wong, et al., "HTS Coils for High Resolution Nuclear Magnetic Resonance Spectroscopy", Advances in Cryogenic Engineering, (1996), pp. 953-959, New York.

V. Kotsubo et al., "Cryogenic System for a High Temperature Superconductor NMR Probe", Advances in Cryogenic Engineering, Jul. 17, 1995, vol. 41, pp. 1857-1864, New York.

Kushida, et al., "Dependence on the Pure Quadrupole Resonance Frequency on Pressure and Temperature", Physical Review, (Dec. 1956), pp. 1364-1377, vol. 104, No. 5, Massachusetts.

Vanier, "Temperature Dependence of the Pure Nuclear Quadrupole Resonance Frequency in KC1O3", Canadian Journal of Physics, (Nov. 1960), pp. 1397-1405, vol. 38, No. 11, Canada.

Smith, et al., "Nitrogen Electric Quadrupole and Proton Magnetic Resonances in Thiourea", Journal of Chemical Physics, (Oct. 1964), pp. 2403-2416, vol. 41, No. 8, New York.

Turner, C.W., High temperature superconductor circuit components for cryogenic microwave systems, Electrical and Computer Engineering, 1993, Canadian Conference on Vancouver, BC Canada (Sep. 14-17, 1993) XP 010118071.

W. A. Edelstein et al., A signal-to-noise calibration procedure for NMR imaging systems, Medical Physics, vol. 11 (2) Mar./Apr. 1984, pp. 180-185.

Hirschfeld, et al., "Short Range Remote NQR Measurements", Journal of Molecular Structure, 1980, pp. 63-77, vol. 58, The Netherlands.

Garroway, et al., "Remote Sensing By Nuclear Quadrupole Resonance", IEEE Transactions on Geoscience and Remote Sensing, Jun. 2001, pp. 1108-1118, vol. 39, No. 6.

Garroway, et al., "Narcotics and Explosives Detection by 14N pure NQR", SPIE, 1993, pp. 318-327, vol. 2092, Maryland.

Charles Wilker, "HTS Sensors for NQR Spectroscopy", vol. 1, pp. 143-146, 2004.

Anders Stensgaard, "Optimized Design of the Shielded-Loop Resonator", Journal of Magnetic Resonance, 122, 120-126 (1996), Article No. 0187.

Ha, D.F. et al., "Metal detector based on high-Tc RF SQUID", Physica C 378-381 (2002) pp. 1404-1407.

Bendall, et. al., "Elimination of Coupling between Cylindrical Transmit Coils and Surface-Receive Coils for in Vivo NMR" Magnetic Resonance in Medicine v3 p. 157-163, 1986.

Black, et al., "A High-Temperature Superconducting Receiver For Nuclear Magnetic Resonance Microscopy", Science, vol. 259, pp. 793-795 Feb. 5, 1993.

Black, et al., "Performance Of A High-Temperature Supercondcuting Resonator For High-Field Imaging", Journal Of Magnetic Resonance, pp. 74-80 (1995).

Colton, et. al., "Making the World a Safer Place", Science, v.299, i.5611, pp. 1324-1325, Feb. 2006.

Fisher, et al., "A Versatile Computer-Controlled Pulsed Nuclear Quadrupole Resonance Spectrometer", Review of Scientific Instruments, v70, No. 12, p. 4678, Dec. 1999.

Hill, "Improved Sensitivity of NMR Spectroscopy Probes By Use Of High-Temperature Superconductive Detection Coils", IEEE Transactions On Applied Superconductivity, vol. 7, pp. 3750-3753, Jun. 1997.

Roemer, et. al., "The NMR Phased Array", Magnetic Resonance In Medicine 16, pp. 192-225, 1990.

Withers, et al., "Thin-Film HTD Probe Coils For Magnetic-Resonance Imaging", IEEE Transactions On Applied Superconductivity, vol. 3, pp. 2450-2453, Mar. 1993.

Landers, et al., "Electronic Effects and Molecular in β-Octahydro-1,3,5,7-tetranitro-1,3,5,7-tetrazocine Bases on $^{14}N$ Nuclear Quadrupole Resonance Spectroscopy", American Chemical Society, J. Phys. Chem., 85, pp. 2618-2623, 1981.

Karpowicz, et. al., "Librational Motion of Hexahydro-1,3,5-trinitro-s-triazine Based on the Temperature Dependence of the Nitrogen-14 Nuclear Quadrupole Resonance Spectra: The Relationship to Condensed-Phase Thermal Decomposition", American Chemical Society, J. Phys. Chem. 87, pp. 2109-2112, 1983.

Volpicelli, et. al., "Locked rf Spectrometer for Nuclear Quadrupole Resonance", The Review of Scientific Instruments, v.25, No. 2, pp. 150-153, Feb. 1965.

Benedek, et al., "Precise Nuclear Resonance Thermometer", The Review of Scientific Instruments, v.28, No. 2, pp. 92-95, Feb. 1957.

Ernst, "Magnetic Resonance with Stochastic Excitation", Journal of Magnetic Resonance 3, pp. 10-27, 1970.

Klainer, et. al., "Fourier Transform Nuclear Quadrupole Resonance Spectroscopy", Fourier, Hadamard, and Hilbert Transforms in Chemistry, pp. 147-182, 1982.

\* cited by examiner $t_1$ $t_2$ $t_3$ $t_4$ $t_1$ $\qquad\qquad\qquad\qquad$ $t_2$ $t_3$ $\qquad\qquad\qquad\qquad$ $t_4$ $t_1$ $\qquad\qquad\qquad\qquad$ $t_2$ $t_3$ $\qquad\qquad\qquad\qquad$ $t_4$

SCANNING A BAND OF FREQUENCIES USING AN ARRAY OF HIGH TEMPERATURE SUPERCONDUCTOR SENSORS TUNED TO THE SAME FREQUENCY This application claims the benefit of U.S. Application No. 60/566,953, filed on Apr. 30, 2004, which is incorporated in its entirety as a part hereof for all purposes.

FIELD OF THE INVENTION

This invention relates to methods and apparatus for scanning a band of frequencies using an array of high temperature superconductor sensors in a nuclear quadrupole resonance detection system.

BACKGROUND OF THE INVENTION

The use of nuclear quadrupole resonance (NQR) as a means of detecting explosives and other contraband has been recognized for some time. See e.g. T. Hirshfield et al, *J. Molec. Struct.* 58, 63 (1980), A. N. Garroway et al, *Proc. SPIE* 2092, 318 (1993), and A. N. Garroway et al, *IEEE Trans. on Geoscience and Remote Sensing* 39, 1108 (2001). NQR provides some distinct advantages over other detection methods. NQR requires no external magnet such as required by nuclear magnetic resonance. NQR is sensitive to the compounds of interest, i.e. there is a specificity of the NQR frequencies.

A detection system can have one or more coils that both transmit and receive, or it can have separate coils that only transmit and only receive. A transmit, or transmit and receive, coil of an NQR detection system provides a radio frequency (RF) magnetic field that excites the quadrupole nuclei in the sample, and results in the production of their characteristic resonance signals that the receive, or transmit and receive, coil (i.e. the sensor) detects. The NQR signals have low intensity and short duration. The transmit, receive, or transmit and receive, coil preferably has a high quality factor (Q). The transmit, receive, or transmit and receive, coil has typically been a copper coil and therefore has a Q of about $10^2$. It can be advantageous to use a transmit, receive, or transmit and receive, coil made of a high temperature superconductor (HTS) rather than copper since the HTS self-resonant coil has a Q of the order of $10^4$-$10^6$.

The large Q of the HTS self-resonant coil plays an important role during reception. In view of the low intensity NQR signal, it is important to have a signal-to-noise ratio (S/N) as large as possible. The signal-to-noise ratio is proportional to the square root of Q so that the use of the HTS self-resonant coil results in an increase in S/N by a factor of 10-100 over that of the copper system. The use of a high temperature superconductor sensor, i.e. receive coil, provides a distinct advantage over the use of an ordinary conductor sensor. The HTS sensor can provide greater sensitivity and/or smaller size.

The performance of a signal detection system can be improved by using an array of sensors, i.e. receive coils, to scan the band of frequencies of interest as compared to using a single sensor. An object of the present invention is to provide method and apparatus for scanning a band of frequencies using an array of sensors in a nuclear quadrupole resonance detection system.

SUMMARY OF THE INVENTION

One embodiment of this invention is a method for scanning a band of frequencies $\Delta F$ with a nuclear quadrupole resonance detection system comprising an array of n high temperature superconductor sensors to detect nuclear quadrupole resonance signals, wherein $n \geq 2$ and the bandwidth of each sensor is $\Delta f$, by (a) determining r different frequencies that span the band of frequencies $\Delta F$ when using sensors with bandwidths $\Delta f$, wherein r is of the order of $\Delta F/\Delta f$;

(b) tuning the resonance frequencies of the n sensors to n different resonance frequencies, wherein the n different resonance frequencies are selected from the group of the r different frequencies, and maintaining these resonance frequencies for a selected period of time;

(c) retuning simultaneously the resonance frequencies of the n sensors to n different frequencies selected from the group of the r different frequencies, and maintaining these retuned resonance frequencies for a selected period of time, wherein each of the n sensors has a retuned resonance frequency that is different from the resonance frequency to which it was tuned or retuned in any previous step; and (d) repeating step (c) r-2 times wherein the resonance frequency of each sensor is tuned for one period of time to each of the r different frequencies, and no two sensors are tuned to the same resonance frequency at the same time.

Steps (b), (c) and (d) may be repeated one or more times, the signals detected by all sensors that are tuned to a selected frequency may be combined, and the periods of time for which the resonance frequencies are maintained in steps (b), (c) and (d) may be the same.

Another embodiment of this invention is a method for scanning a band of frequencies $\Delta F$ with a nuclear quadrupole resonance detection system comprising an array of n high temperature superconductor sensors to detect nuclear quadrupole resonance signals, wherein $n \geq 4$ and the bandwidth of each sensor is $\Delta f$, by (a) dividing the sensors into m groups with p sensors in each group, determining r different frequencies that span the band of frequencies $\Delta F$ when using sensors with bandwidths $\Delta f$, wherein r is of the order of $\Delta F/\Delta f$, dividing the r different frequencies into s sets with p of the r different frequencies in each set, and assigning each set of frequencies to one of the groups of sensors;

(b) tuning the resonance frequencies of the p sensors in each group to the p different frequencies in the set of frequencies assigned to that group, and maintaining these tuned resonance frequencies for a selected period of time;

(c) retuning simultaneously the resonance frequencies of the p sensors in each group to p different frequencies within the same set assigned to that group for step (b), and maintaining these retuned resonance frequencies for a selected period of time, wherein each of the p sensors has a retuned resonance frequency that is different from the resonance frequency to which it was tuned or retuned in any previous step;

(d) repeating step (c) p-2 times;

(e) retuning the resonance frequencies of the p sensors in each group to the p different frequencies in a second set of frequencies assigned to that group, and maintaining these retuned resonance frequencies for a selected period of time;

(f) retuning simultaneously the resonance frequencies of the p sensors in each group to p different frequencies within the same set assigned to that group for step (e), and maintaining these retuned resonance frequencies for a selected period of time, wherein each of the p sensors has a retuned resonance frequency that is different from the resonance frequency to which it was tuned or retuned in any previous step;

(g) repeating step (f) p-2 times; and (h) repeating steps (e), (f) and (g) for each additional set of p different frequencies until all s sets of frequencies have been used as resonance frequencies for one of the m groups of sensors.

Steps (b) through (h) may be repeated one or more times, the signals detected by all sensors that are tuned to a selected frequency may be combined, and the periods of time for which the resonance frequencies are maintained in steps (b) through (h) may be the same.

A further embodiment of this invention is a method for scanning a band of frequencies $\Delta F$ with a nuclear quadrupole resonance detection system comprising an array of n high temperature superconductor sensors to detect nuclear quadrupole resonance signals, wherein $n \geq 4$ and the bandwidth of each sensor is $\Delta f$, by (a) dividing the n sensors into m groups with p sensors in each group, determining r different frequencies that span the band of frequencies $\Delta F$ when using sensors with bandwidths $\Delta f$, wherein r is of the order of $\Delta F/\Delta f$, dividing the r different frequencies into m sets with at least p of the r different frequencies in each set, and assigning one set of frequencies to each group of sensors;

(b) tuning the resonance frequencies of the p sensors in each group to p different frequencies selected from any of the frequencies assigned to that group, and maintaining these tuned resonance frequencies for a selected period of time;

(c) retuning simultaneously the resonance frequencies of the p sensors in each group to p different frequencies selected from any of frequencies assigned to that group, and maintaining these retuned resonance frequencies for a selected period of time, wherein each of the p sensors has a retuned resonance frequency that is different from the resonance frequency to which it was tuned or retuned in any previous step; and (d) repeating step (c) until all of the frequencies in the sets of frequencies assigned to each group have been used as a resonance frequency by each sensor in the group.

Steps (b), (c) and (d) may be repeated one or more times, the signals detected by all sensors that are tuned to a selected frequency may be combined, and the periods of time for which the resonance frequencies are maintained in steps (b), (c) and (d) may be the same.

Yet another embodiment of this invention is a nuclear quadrupole resonance detection system for scanning a sample, comprising (a) n high temperature superconductor sensors, each with bandwidth $\Delta f$, to scan a band of frequencies $\Delta F$ and detect any nuclear quadrupole resonance signal within the band of frequencies $\Delta F$, wherein $n \geq 2$;

(b) means to tune the resonance frequencies of the n sensors to n different frequencies, wherein the n different frequencies are selected from the group of r different frequencies that span the band of frequencies $\Delta F$ using sensors with bandwidths $\Delta f$, and wherein r is of the order of $\Delta F/\Delta f$; and (c) means to simultaneously retune r-1 times the resonance frequencies of the n sensors to n different frequencies each time, wherein after each retuning, each of the n sensors has a retuned resonance frequency that is different from any of the resonance frequencies to which it was previously tuned or retuned.

Yet another embodiment of this invention is a method for scanning a band of frequencies $\Delta F$ with a nuclear quadrupole resonance detection system comprising an array of n high temperature superconductor sensors to detect nuclear quadrupole resonance signals, wherein $n \geq 2$ and the bandwidth of each sensor is $\Delta f$, by (a) determining r different frequencies that span the band of frequencies $\Delta F$ when using sensors with bandwidths $\Delta f$, wherein r is of the order of $\Delta F/\Delta f$;

(b) tuning the resonance frequencies of the n sensors to n different frequencies, wherein the n different frequencies are selected from the group of the r different frequencies, and maintaining the resonance frequencies of the n sensors for a selected period of time;

(c) retuning the resonance frequencies of some or all of the n sensors to any of the r different frequencies that were not used in any previous step, wherein the n sensors have n different resonance frequencies, and maintaining the resonance frequencies of the n sensors for a selected period of time; and (d) repeating step (c) until all the r different frequencies have been used as resonance frequencies.

Steps (b), (c) and (d) may be repeated one or more times, the signals detected by all sensors that are tuned to a selected frequency may be combined, the periods of time for which the resonance frequencies are maintained in steps (b), (c) and (d) may be the same, and in step (c) the resonance frequencies of all of the n sensors are retuned to any of the r different frequencies that were not used in any previous step.

Yet another embodiment of this invention is a nuclear quadrupole resonance detection system for scanning a sample, comprising:

(a) n high temperature superconductor sensors, each with bandwidth $\Delta f$, to scan a band of frequencies $\Delta F$ and detect any nuclear quadrupole resonance signal within the band of frequencies $\Delta F$, wherein $n \geq 2$;

(b) means to tune the resonance frequencies of the n sensors to n different frequencies, wherein the n different frequencies are selected from the group of r different frequencies that span the band of frequencies $\Delta F$ using sensors with bandwidths $\Delta f$, and wherein r is of the order of $\Delta F/\Delta f$; and (c) means to simultaneously retune the resonance frequencies of the n sensors to n different frequencies that are not any of the r different frequencies used previously as resonance frequencies, and to continue to retune the n sensors in the same manner until all the r different frequencies have been used as resonance frequencies.

Yet another embodiment of this invention is a nuclear quadrupole resonance detection system for scanning a sample, comprising:

(a) n high temperature superconductor sensors, each with bandwidth $\Delta f$, to scan a band of frequencies $\Delta F$ and detect any nuclear quadrupole resonance signal within the band of frequencies $\Delta F$, wherein $n \geq 2$; and (b) means to tune the resonance frequencies of each of the n sensors to r different frequencies, wherein the r different frequencies span the band of frequencies $\Delta F$ using sensors with bandwidths $\Delta f$ and wherein r is of the order of $\Delta F/\Delta f$.

Yet another embodiment of this invention is a method for scanning a band of frequencies $\Delta F$ with a nuclear quadrupole resonance detection system comprising an array of n high temperature superconductor sensors to detect nuclear quadrupole resonance signals, wherein $n \geq 2$ and the bandwidth of each sensor is $\Delta f$, by (a) determining r different frequencies that span the band of frequencies $\Delta F$ when using sensors with bandwidths $\Delta f$, wherein r is the order of $\Delta F/\Delta f$;

(b) tuning the resonance frequencies of all the n sensors to the same frequency, wherein the frequency is selected from the group of the r different frequencies, and maintaining the resonance frequencies for a selected period of time;

(c) retuning simultaneously the resonance frequencies of all of the n sensors to the same frequency, wherein the retuned frequency is another of the r different frequencies, and maintaining these retuned resonance frequencies for a selected period of time; and (d) repeating step (c) r-2 times, wherein after each retuning the retuned resonance frequencies of the n sensors are different from the resonance frequencies to which the sensors are tuned or retuned in any of the previous steps.

Steps (b), (c) and (d) may be repeated one or more times, the signals detected by all sensors that are tuned to a selected frequency may be combined, and the periods of time for which the resonance frequencies are maintained in steps (b), (c) and (d) may be the same.

Yet another embodiment of this invention is a nuclear quadrupole resonance detection system for scanning a sample, comprising:

(a) n high temperature superconductor sensors, each with bandwidth $\Delta f$, to scan a band of frequencies $\Delta F$ and detect any nuclear quadrupole resonance signal within the band of frequencies $\Delta F$, wherein $n \geq 2$;

(b) means to tune the resonance frequencies of all the n sensors to the same resonance frequency, wherein the resonance frequency is selected from the group of r different frequencies that span the band of frequencies $\Delta F$ using sensors with bandwidths $\Delta f$, and wherein r is of the order of $\Delta F/\Delta f$; and (c) means to simultaneously retune r-1 times the resonance frequencies of all the n sensors to the same frequency each time, wherein the frequency each time is another of the r different frequencies, and wherein after each retuning each of the n sensors has a retuned resonance frequency that is different from any resonance frequencies to which it has previously been retuned.

The methods of the invention for scanning a band of frequencies in a nuclear quadrupole resonance detection system are especially useful when the nuclear quadrupole resonance detection system is being used for detecting the nuclear quadrupole resonance of explosives, drugs and other contraband.

DETAILED DESCRIPTION OF THE PREFERRED EMBODIMENTS

This invention provides methods for scanning a band of frequencies in a NQR detection system. This invention also provides NQR detection systems that can accomplish these improved performances.

The high Q and relatively small size of an HTS sensor makes the use of an array of such sensors feasible, and the method of scanning this array is critical to the performance of the NQR detection system using the array. There are various reasons that would make scanning a band of frequencies desirable in a NQR detection system. One motivation for such scanning arises from the temperature dependence of NQR frequencies. The temperature of the sample to be scanned as a source of NQR may be known only within some range of temperature. As a result, the NQR frequency is known only within a range of frequencies, i.e. a band of frequencies. To detect the NQR signal there must be detection capability over the band of frequencies. Another reason for scanning a band of frequencies is to search for more than one NQR frequency.

Figure 1:
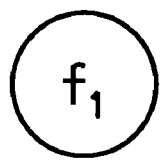
FIG. 1 shows one embodiment for scanning a band of frequencies using an array of four sensors wherein all four sensors have the same resonance frequency at any given time and are stepped in unison through the frequency band.
Figure 1:
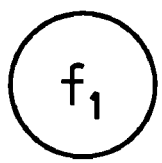
Figure 1:
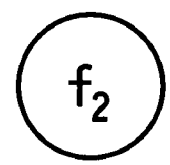
Figure 1:
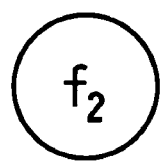
Figure 1:
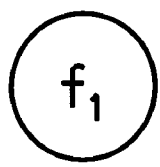
Figure 1:
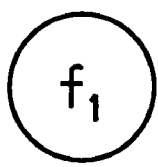
Figure 1:
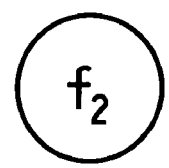
Figure 1:
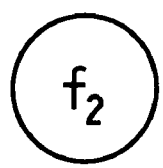
Figure 1:
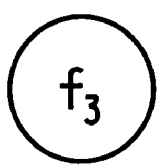
Figure 1:
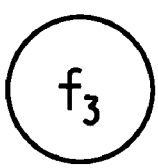
Figure 1:
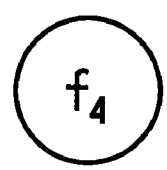
Figure 1:
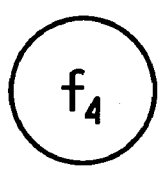
Figure 1:
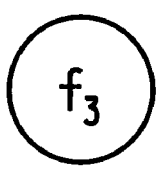
Figure 1:
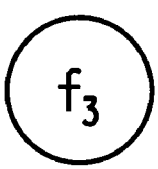
Figure 1:
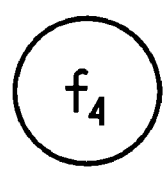
Figure 1:
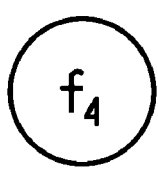

One method to carry out such a scan comprises tuning all the sensors in the array to the same frequency, a selected frequency within the band, and then frequency stepping all of the sensors in the array, i.e. changing the resonance frequencies of all the sensors in the array in the same manner. This method is illustrated in FIG. 1 with an array of four sensors. For simplicity, four frequency settings $f_1$, $f_2$, $f_3$ and $f_4$ are assumed to span the frequency band of interest. FIG. 1 illustrates the method and shows the resonance frequencies of the four sensors at four different times $t_1$, $t_2$, $t_3$ and $t_4$. Since the resonance frequencies of the sensors are stepped through the band of frequencies in the same way, all four sensors have the same resonance frequency at any given time.

As described above, it is advantageous for sensors to have the high Q of the high temperature superconductor sensors used in this invention. With the high Q, there is a corresponding narrow bandpass, i.e. the bandwidth of the sensor $\Delta f = f_R/Q$, where $f_R$ is the resonance frequency. The number of different frequencies r that span the band of frequencies $\Delta F$ when using sensors with bandwidths $\Delta f$ is of the order of $\Delta F/\Delta f$. The ratio $\Delta F/\Delta f = w$, where w is the minimum number of frequencies spanning the band of frequencies $\Delta F$ when scanning with sensors of bandwidths $\Delta f$, i.e. to span the band of frequencies, the sensors must be tuned to at least w different frequencies. It may be advantageous to increase the number of frequencies used to increase the sensitivity of the measurements. As used herein, "the r different frequencies that span the band of frequencies $\Delta F$ when using sensors with bandwidths $\Delta f$, wherein r is of the order of $\Delta F/\Delta f$" means that r is at least equal to w, and can be up to three times w.

In view of the narrow bandpass $\Delta f$ and depending on n, the number of sensors in the array, and the width $\Delta F$ of the band of frequencies to be scanned, r may be greater than n. This method of scanning then comprises initially tuning all n sensors to the same frequency where that frequency is selected from the group of r different frequencies. The resonance frequencies of all n sensors are then simultaneously retuned r-1 times, wherein the resonance frequency of all the sensors each time is another of the r different frequencies, and wherein after each retuning the retuned resonance frequencies of the n sensors are different from the resonance frequencies used in any of the previous retunings. Upon completion of the r-1 retunings, all r different frequencies have been used as resonance frequencies. The r different frequencies do not have to be used as resonance frequencies in any particular order. While the sensors will typically be made as essentially identical as possible, there will be some small variation in properties from sensor to sensor, including in $\Delta f$.

In many NQR detection systems, the sensors will be closely spaced. There is a coupling between these sensors as a result of the mutual inductance between them. This coupling between two sensors increases as the distance between them decreases. The problem of the coupling between sensors is exacerbated when using HTS sensors because of the very large Q's of the HTS sensors. This coupling of sensors can have serious effects on the performance of the NQR detection system. When the sensors are so closely spaced that coupling interferes with detection system performance, it is preferred to employ a device to decouple the sensors. If a device to decouple the sensors is not employed, however, it would be preferable to use one of the methods of the invention for scanning a band of frequencies described below instead of the method described above in which all the n sensors have the same resonance frequency.

Figure 2:
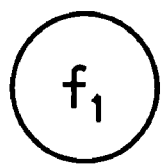
FIG. 2 shows a second embodiment for scanning a band of frequencies using an array of four sensors wherein the resonance frequencies are initially set at four different frequencies and kept fixed at those frequencies.
Figure 2:
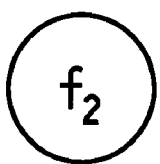
Figure 2:
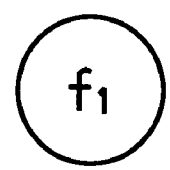
Figure 2:
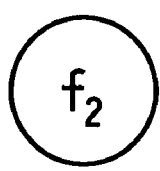
Figure 2:
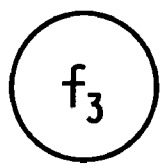
Figure 2:
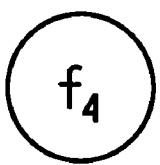
Figure 2:
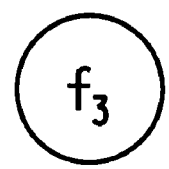
Figure 2:
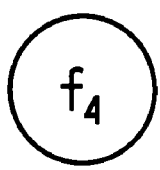
Figure 2:
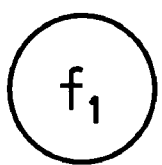
Figure 2:
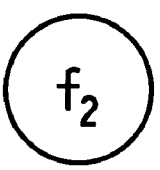
Figure 2:
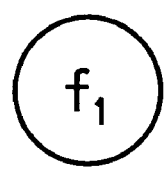
Figure 2:
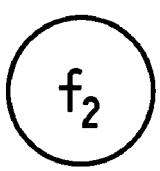
Figure 2:
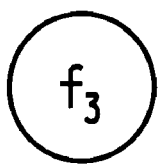
Figure 2:
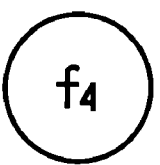
Figure 2:
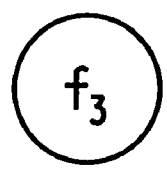
Figure 2:
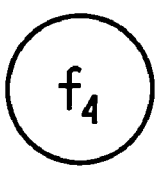

One such alternative method to scan a band of frequencies of interest comprises having n sensors in the array with each having a different resonance frequency. The method is illustrated in FIG. 2. For simplicity and comparison, an array of four sensors and the same four frequencies $f_1$, $f_2$, $f_3$ and $f_4$ used in FIG. 1 are used again in FIG. 2. The four frequencies are again assumed to span the frequency band of interest. FIG. 2 shows the resonance frequencies of the four sensors at four different times $t_1$, $t_2$, $t_3$ and $t_4$. The resonance frequencies are initially set at four different frequencies and kept fixed at those frequencies. For those situations, in which r is greater than n as discussed above, the resonance frequencies of the n sensors are first tuned to n different frequencies selected from the group of r different frequencies. The resonance frequencies of some or all of the n sensors are then retuned to any of the r different frequencies that were not used previously. Preferably, all of the n sensors are retuned. The retuning is continued until all r frequencies are used as resonance frequencies. Coupling can be further reduced by choosing the n different frequencies, and the sensors with these resonance frequencies, such that, to the extent possible, frequencies are selected that are not too close in frequency and the closer frequencies are spatially separated. While coupling can be reduced by this method, combining the signals from different sensors to achieve noise reduction may have reduced effectiveness, and the spatial sensitivity of the array is limited.

Figure 3:
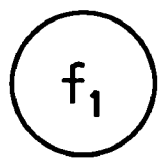
FIG. 3 shows another embodiment of the invention for scanning a band of frequencies using an array of four sensors wherein the resonance frequencies are initially set at four different frequencies, and the resonance frequencies are then simultaneously retuned to the four different frequencies at 3 subsequent times, wherein each of the four sensors has a retuned resonance frequency that is different from any of its previous resonance frequencies.
Figure 3:
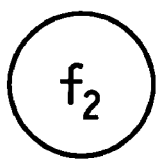
Figure 3:
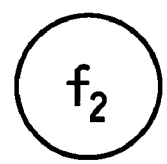
Figure 3:
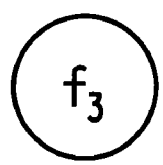
Figure 3:
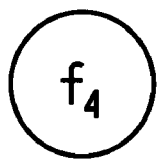
Figure 3:
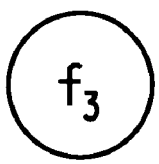
Figure 3:
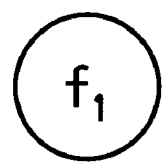
Figure 3:
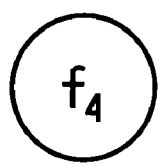
Figure 3:
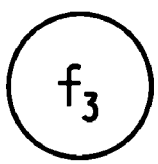
Figure 3:
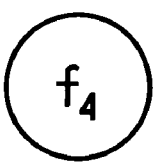
Figure 3:
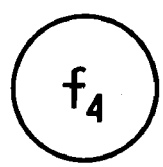
Figure 3:
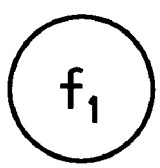
Figure 3:
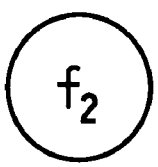
Figure 3:
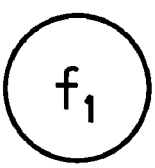
Figure 3:
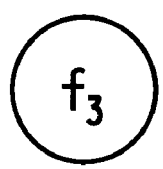
Figure 3:
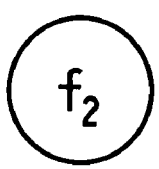

In another embodiment that provides excellent spatial sensitivity and reduced coupling, the method comprises tuning the resonance frequencies of the n high temperature superconductor sensors to n different frequencies, and retuning the resonance frequencies of all of the sensors r-1 times. The resonance frequencies of the n sensors are always different, and the same resonance frequency is used only once for each sensor. At the conclusion of the r-1 retunings, all of the r different frequencies will have been used as resonance frequencies for each of the n sensors. This method is illustrated in FIG. 3 using the same array of four sensors and four frequencies used in FIGS. 1 and 2. FIG. 3 shows the resonance frequencies of the four sensors at four different times $t_1$, $t_2$, $t_3$ and $t_4$. The resonance frequencies of the four sensors are initially set at four different frequencies $f_1$, $f_2$, $f_3$ and $f_4$. These four frequencies are assumed to span the frequency band of interest. The resonance frequencies are maintained for a selected period of time and are then simultaneously retuned to the four different. frequencies. This simultaneous retuning is repeated two more times with the proviso that each of the four sensors has a retuned resonance frequency that is different from any of its previous resonance frequencies. At the completion of the retunings, each of the sensors has had its resonance frequency set at each of the four frequencies, and each of the frequencies was maintained for the selected period of time. The four times $t_1$, $t_2$, $t_3$ and $t_4$ represent a time in each of the four given time periods. The four frequencies are shown rotated counter-clockwise among the four sensors in FIG. 3, but various assignments of frequencies can be used.

When this method is applied in those situations in which r is greater than n as discussed above, the resonance frequencies of the n sensors are first tuned to n different frequencies selected from the group of r different frequencies. The resonance frequencies of the n sensors are then simultaneously retuned to n different frequencies selected from the group of r different frequencies. Each of the n sensors has a retuned resonance frequency that is different from its previously tuned or retuned resonance frequency. The retuning step is repeated r-2 times, wherein each of the n sensors has a retuned resonance frequency that is different from its resonance frequency in any of the previous steps and wherein some or all of the n frequencies selected in any retuning step may be different from the n frequencies selected for the previous tuning. It is desirable to have those sensors with nearest resonance frequencies spatially separated. This is more readily accomplished as the number of sensors in the array increases. This method of the invention further comprises combining the signals detected by the n sensors when their resonance frequencies were tuned to the same frequency to thereby improve the signal-to-noise ratio.

In another embodiment, the method comprises using an array of n high temperature superconductor sensors wherein $n \geq 4$. The method comprises dividing the n sensors into m groups with p sensors in each group, dividing the r different frequencies that span the band of frequencies into s sets with p of the r different frequencies in each set, and assigning each set of frequencies to one of the groups of sensors. In the typical situation in which this method would be employed, r would be greater than n so that s would be greater than m, and some or all of the m groups of sensors would be assigned two or more of the s sets of frequencies. The resonance frequencies of the p sensors in each group are tuned to the p different frequencies in a set assigned to that group. The resonance frequencies of the p sensors in each group are then simultaneously retuned to p different frequencies within the same set previously assigned to that group. Each of the p sensors has a retuned resonance frequency that is different from the resonance frequency to which it was previously tuned or retuned. The retuning step is repeated p-2 times, wherein each of the p sensors in each group has a retuned resonance frequency that is different from the resonance frequency used for it in any of the previous steps.

The resonance frequencies of the p sensors in each group are then simultaneously retuned to p different frequencies in a second set of frequencies assigned to that group. The resonance frequencies of the p sensors in each group are then simultaneously retuned to p different frequencies in the same second set of frequencies used previously for that group. Each of the p sensors has a retuned resonance frequency that is different from any resonance frequency to which it was previously tuned or retuned. The retuning step is repeated p-2 times, wherein each of the p sensors in each group has a retuned resonance frequency that is different from the resonance frequency used for it in any of the previous steps. Retuning is continued until all s sets of frequencies have been used as resonance frequencies by one of the m groups of sensors. This method further comprises combining the signals detected by the p sensors in each group when their resonance frequencies were tuned to the same frequency to thereby improve the signal-to-noise ratio.

Alternatively, the r different frequencies are divided into m sets with at least p of the r different frequencies in each set. One set of frequencies is assigned to each group of sensors. The resonance frequencies of the p sensors in each group are tuned to p different frequencies selected from any of the frequencies assigned to that group. The resonance frequencies of the p sensors in each group are retuned to p different frequencies selected from any of frequencies assigned to that group. Each of the p sensors has a retuned resonance frequency that is different from the resonance frequency used for it in any previous step. The retuning step is repeated until all of the frequencies in the sets of frequencies assigned to each group have been used as a resonance frequency by each sensor in the group.

Tuning or retuning the resonance frequency of a sensor may be accomplished in a variety of ways. Means for tuning and/or retuning the resonance frequency of a sensor may include, for example, using two or more movable, coupled high temperature superconductor self-resonant coils. The resonance frequency of the fundamental symmetric mode of the two or more coupled high temperature superconductor self-resonant coils can then be varied by mechanically displacing one or more coils with respect to the others, and these coupled coils as mechanically adjusted will serve as the HTS sensor coil. Preferably, the two or more coils are planar, i.e. surface, coils. Each planar coil can have a HTS coil configuration on only one side of the substrate or essentially identical HTS coil configurations on both sides of the substrate. Preferably, the HTS sensors are each comprised of a high temperature superconductor self-resonant planar coil or two or more coupled high temperature superconductor self-resonant planar coils.

Alternatively, for a sensor comprised of a high temperature superconductor self-resonant coil or two or more coupled high temperature superconductor self-resonant coils, means for tuning and/or retuning the resonance frequency of the sensor to a specified frequency may include a circuit, preferably one for each sensor. The circuit is comprised of a single loop or coil to inductively couple the circuit to the high temperature superconductor self-resonant sensor, a reactance in series with the single loop or coil, and means to connect the reactance to, and disconnect the reactance from, the single loop or coil. The single loop or coil can be made of a regular conductor such as copper or a high temperature superconductor. The reactance can be an inductance, capacitance or combination of both. Means to connect the reactance to, and disconnect the reactance from, the single loop or coil may include at least one mechanical switch or electrical switch such as a diode. Preferably, the reactance can be varied so that the resonance frequency can be adjusted to more than one frequency. A variable reactance may be provided where the reactance is comprised of two or more capacitors in parallel, each of which can be individually connected to or disconnected from the single loop or coil. Alternatively, a variable reactance may be comprised of two or more inductors in series, each of which can be individually connected to or disconnected from the single loop or coil by a mechanical or electrical switch that can short-circuit the inductor and thereby essentially remove it from the circuit.

This invention thus provides a nuclear quadrupole resonance detection system for scanning a sample. The detection system is comprised of n high temperature superconductor sensors to scan a band of frequencies and detect any nuclear quadrupole resonance signal within the band of frequencies. The detection system also comprises means to tune and/or retune the resonance frequencies of the n sensors to r different frequencies, wherein the r different frequencies span the band of frequencies. As indicated above, means for tuning and/or retuning may include a circuit comprised of a single loop or coil to inductively couple the circuit to the high temperature superconductor self-resonant sensor, a reactance in series with the single loop or coil, and means to connect the reactance to and disconnect the reactance from the single loop or coil. When two or more coupled high temperature superconductor self-resonant coils are used as a sensor, means for tuning and/or retuning the resonance frequency may include micropositioners to mechanically displace one or more coils with respect to the others. In addition, the detection system is comprised of means to simultaneously retune the resonance frequencies of the n sensors. Means to simultaneously retune the n sensors may include those described above for the initial tuning.

This nuclear quadrupole resonance detection system further comprises means to combine the signals detected by the n sensors when their resonance frequencies were tuned to the same frequency to thereby improve the signal-to-noise ratio. The NQR signals detected by all sensors tuned to a selected resonance frequency can be combined in various ways to enhance detection system performance. For example, means to combine signals may include a programmed microprocessor to add the signals coherently, i.e. the phases of the individual signals are adjusted to add constructively, by various analog and digital techniques. In the analog technique for coherent addition, the electrical path from each sensor to the combination point, at which the signals are added, is adjusted so that the signals add constructively at the combination point. When the sensors are essentially equidistant from the sample that is the source of the nuclear quadrupole resonance signal, the electrical paths from the sensors to the combination point can be made essentially identical thereby insuring that the signals add constructively at the combination point. In the digital technique for coherent addition, each signal detected by the sensors is multiplied, before combination, by a constant complex factor that can be measured or calculated to correct for phase differences between the signal paths and thereby insure that the signals add constructively at the combination point. The constant complex factor is specific to each electrical path from each sensor to the combination point. Typically, the signals will be amplified before they are added.

The advantages of combining signals can be seen as follows. The signal S obtained by coherently adding the signals from n sensors is proportional to n. Assuming that the noise present is random, the noise N, after the coherent addition, is proportional to $n^{0.5}$. Therefore S/N is proportional to $n^{0.5}$, i.e. the square root of n. The combination of signals from two sensors therefore increases S/N by a factor of 1.4. The combination of signals from four sensors increases S/N by a factor of 2.

The sensors used to detect the nuclear quadrupole resonance signals can be used only as receive coils, or as both transmit and receive coils. Preferably, separate coils are used to transmit the RF signal and to detect any NQR signals, and the sensors are thus used solely as receive coils, i.e. they solely detect the nuclear quadrupole resonance signals and are not used to transmit an excitation signal.

The transmit coils used in this invention can be made of normal metals such as copper, silver and aluminum, or can be made from a high temperature superconductor. A normal metal coil is preferably in the form of a shielded-loop resonator (SLR) coil. SLRs have been developed to eliminate the detuning effect of the electrical interaction between the coil and the surrounding material.

Preferably, one or more SLR copper transmit coils are used to apply an RF signal to the sample to be scanned. Preferably, the sensors are high temperature superconductor (HTS) coils in the form of a self-resonant planar coil, i.e. a surface coil, with a coil configuration of HTS on only one side of the substrate or essentially identical HTS coil configurations on both sides of the substrate. High temperature superconductors are those that superconduct above 77K. The high temperature superconductors used to form the HTS self-resonant coil are preferably selected from the group consisting of $YBa_2Cu_3O_7$, $Tl_2Ba_2CaCu_2O_8$, $TlBa_2Ca_2Cu_3O_9$, $(TlPb)Sr_2CaCu_2O_7$ and $(TlPb)Sr_2Ca_2Cu_3O_9$. Most preferably, the high temperature superconductor is $YBa_2Cu_3O_7$ or $Tl_2Ba_2CaCu_2O_8$.

An HTS self-resonant coil can be formed by various known techniques. Preferably, a planar coil is formed by first depositing HTS layers on both sides of a single crystal substrate. In a preferred technique for forming a $Tl_2Ba_2CaCu_2O_8$ coil, the HTS layers are formed directly on a single crystal $LaAlO_3$ substrate or on a $CeO_2$ buffer layer on a single crystal sapphire ($Al_2O_3$) substrate. An amorphous precursor layer of Ba:Ca:Cu oxide about 500 nm thick and with a stoichiometry of about 2:1:2 is deposited by off-axis magnetron sputtering from a Ba:Ca:Cu oxide target. The precursor film is then thallinated by annealing it in air for about 45 minutes at 850° C. in the presence of a powder mixture of $Tl_2Ba_2Ca_2Cu_3O_{10}$ and $Tl_2O_3$. When this powder mixture is heated, $Tl_2O$ evolves from the powder mixture, diffuses to the precursor film and reacts with it to form the $Tl_2Ba_2CaCu_2O_8$ phase. The sample is then coated with photoresist on both sides and baked.

A coil design mask is prepared. The design mask is then centered on the photoresist covering the $Tl_2Ba_2CaCu_2O_8$ film on the front side of the substrate and exposed to ultraviolet light. If the coil is to have the same HTS pattern on both sides of the substrate, the design mask is then centered on the photoresist covering the $Tl_2Ba_2CaCu_2O_8$ film on the back side of the substrate and exposed to ultraviolet light. The resist is then developed and the portion of the $Tl_2Ba_2CaCu_2O_8$ film exposed when the resist is developed is etched away by argon beam etching. The remaining photoresist layer is then removed by an oxygen plasma. The result is the desired HTS planar coil. If two or more coupled high temperature superconductor self-resonant coils are to be used as the sensor coil, additional coils can be produced using the same technique.

Provision must be made in the detection system of this invention for a power supply to supply power for transmitting an RF excitation pulse. Provision must also be made for cooling the HTS materials to at least liquid nitrogen temperature.

An NQR detection system comprised of an array of two or more high temperature superconductor sensors can be used to detect the presence of chemical compounds for any purpose, but is particularly useful for detecting the presence of controlled substances such as explosives, drugs or contraband of any kind. Such an NQR detection system could be usefully incorporated into a safety system, a security system, or a law enforcement screening system. Such systems would typically include a mechanical system for automatically moving objects to be scanned into and out of the range of the scanner, and may also include an enclosure in which objects to be subjected to NQR scanning could be placed and shielded from the environment during the test. Where such an enclosure is used, the mechanical system would automatically moving objects to be scanned into and out of the enclosure.

Where an apparatus or method of this invention is stated or described as comprising, including, containing, having, being composed of or being constituted by certain components or steps, it is to be understood, unless the statement or description explicitly provides to the contrary, that one or more components or steps other than those explicitly stated or described may be present in the apparatus or method. In an alternative embodiment, however, the apparatus or method of this invention may be stated or described as consisting essentially of certain components or steps, in which embodiment components or steps that would materially alter the principle of operation or the distinguishing characteristics of the apparatus or method would not be present therein. In a further alternative embodiment, the apparatus or method of this invention may be stated or described as consisting of certain components or steps, in which embodiment components or steps other than those as stated or described would not be present therein.

Where the indefinite article "a" or "an" is used with respect to a statement or description of the presence of a component in an apparatus, or a step in a method, of this invention, it is to be understood, unless the statement or description explicitly provides to the contrary, that the use of such indefinite article does not limit the presence of the component in the apparatus, or of the step in the method, to one in number.

What is claimed is:

1. A method for detecting the presence of nuclear guadrapole resonance signals in a sample by scanning the sample with a band of frequencies $\Delta F$ using a nuclear quadrupole resonance detection system comprising an array of n high temperature superconductor sensors, wherein $n \geq 2$ and the bandwidth of each sensor is $\Delta f$, the method comprising the steps of:
 a) determining r different frequencies that span the band of frequencies $\Delta F$ when using sensors with bandwidths $\Delta f$, wherein r is the order of $\Delta F/\Delta f$;
 b) tuning the resonance frequency of all the n sensors to the same frequency, wherein the frequency is selected from the group of the r different frequencies, and maintaining the resonance frequencies for a selected period of time;
 c) retuning simultaneously the resonance frequency of all the n sensors to the same frequency, wherein the retuned frequency is another of the r different frequencies, and maintaining these retuned resonance frequencies for a selected period of time; and
 d) repeating step (c) r-2 times, wherein after each retuning the retuned resonance frequencies of the n sensors are different from the resonance frequencies to which the sensors are tuned or retuned in any of the previous steps whereby every one of the r frequencies is used by every one of the sensors to scan the sample for the presence of nuclear quadrapole resonance signals.

2. The method of claim 1, further comprising the step of repeating steps (b), (c) and (d) one or more times.

3. The method of claim 1, further comprising the step of combining the signals detected by all sensors that are tuned to a selected frequency.

4. The method of claim 1, wherein each resonance frequency is maintained for the same period of time.

5. The method of claim 1, wherein the n high temperature superconductor sensors solely detect the presence of nuclear quadrupole resonance signals.

6. The method of claim 5, wherein each high temperature superconductor sensor is comprised of a high temperature superconductor self-resonant planar coil.

7. The method of claim 5, wherein each high temperature superconductor sensor is comprised of two or more coupled high temperature superconductor self-resonant planar coils.

8. A nuclear quadrupole resonance detection system configured for scanning a sample, comprising:
  a) n high temperature superconductor sensors, each with bandwidth $\Delta f$, in order to scan a band of frequencies $\Delta F$ and detect any nuclear quadrupole resonance signal within the band of frequencies $\Delta F$, wherein $n \geq 2$;
  b) means to tune the resonance frequencies of all the n sensors to the same resonance frequency, wherein the resonance frequency is selected from the group of r different frequencies that span the band of frequencies $\Delta F$ using sensors with bandwidths $\Delta f$, and wherein r is of the order of $\Delta F/\Delta f$; and
  c) means to simultaneously retune r-1 times the resonance frequencies of all the n sensors to the same frequency each time, wherein the frequency each time is another of the r different frequencies, and wherein after each retuning each of the n sensors has a retuned resonance frequency that is different from any resonance frequencies to which it has previously been retuned.

9. The nuclear quadrupole resonance detection system of claim 8, further comprising:
  d) means to combine the signals detected by all sensors that are tuned to a selected frequency.

10. The nuclear quadrupole resonance detection system of claim 8, wherein the n high temperature superconductor sensors solely detect nuclear quadrupole resonance signals.

11. The nuclear quadrupole resonance detection system of claim 10, wherein each high temperature superconductor sensor is comprised of a high temperature superconductor self-resonant planar coil.

12. The nuclear quadrupole resonance detection system of claim 10, wherein each high temperature superconductor sensor is comprised of two or more coupled high temperature superconductor self-resonant planar coils.

13. The nuclear quadrupole resonance detection system of claim 10, further comprising one or more shielded-loop resonator coils In order to apply to the sample to be scanned for the presence of nuclear quadrupole resonance an RF signal capable of exciting quadrupolar nuclei in the sample.

14. The nuclear quadrupole resonance detection system of claim 10, wherein the means to tune and simultaneously retune the resonance frequency of each of the n sensors is comprised of n circuits, one for each of the n sensors, wherein each circuit is comprised of (a) a single loop or coil to inductively couple the circuit to the high temperature superconductor self-resonant sensor, (b) a variable reactance in series with the single loop or coil, and (c) means to connect the variable reactance to, and disconnect the variable reactance from, the single loop or coil.

15. The nuclear quadrupole resonance detection system of claim 10, wherein the means to tune and simultaneously retune the resonance frequency of each of the n sensors is comprised of one or more circuits that is comprised of a variable reactance.

16. The nuclear quadrupole resonance detection system of claim 8, wherein the sample comprises explosives, drugs or other contraband.

17. The nuclear quadrupole resonance detection system of claim 9, wherein the sample comprises explosives, drugs or other contraband.

18. A safety system, a security system, or a law enforcement screening system comprising the nuclear quadrupole resonance detection system of claim 9.

* * * * *